United States Patent [19]

Matsumura et al.

[11] Patent Number: 5,433,106
[45] Date of Patent: Jul. 18, 1995

[54] METHOD FOR DETECTING MOISTURE IN A HONEYCOMB PANEL

[75] Inventors: Hiroyuki Matsumura, Kobe; Takamasa Ogata, Kobe; Hideyuki Hirasawa, Kobe; Masato Uchiyama, Minokamo; Kenji Tsubaki, Kakamigahara, all of Japan

[73] Assignee: Kawasaki Jukogyo Kaisha, Hyogo, Japan

[21] Appl. No.: 46,992

[22] Filed: Apr. 16, 1993

[30] Foreign Application Priority Data

Apr. 20, 1992 [JP] Japan ................... 4-128233

[51] Int. Cl.⁶ .......................................... G01N 25/56
[52] U.S. Cl. ........................... 73/75; 374/124; 374/45
[58] Field of Search ............ 73/73, 75; 374/4, 5, 374/45, 124

[56] References Cited

U.S. PATENT DOCUMENTS

| | | | |
|---|---|---|---|
| 3,034,334 | 5/1962 | DeForest | 374/5 |
| 3,216,241 | 11/1965 | Hansen | 73/75 |
| 3,504,524 | 4/1970 | Maley | 374/5 |
| 3,566,669 | 3/1971 | Lawrence et al. | 374/5 |
| 3,681,970 | 8/1972 | Wells | 374/5 |
| 4,532,797 | 8/1985 | Yang | 73/75 |
| 4,612,802 | 9/1986 | Clarke et al. | 73/75 |
| 4,647,220 | 3/1987 | Adams | 374/5 |
| 4,762,426 | 8/1988 | Foss | 73/335.01 X |
| 4,845,978 | 7/1989 | Whitford | 73/75 |
| 4,913,558 | 4/1990 | Wettervik et al. | 374/4 |
| 4,965,451 | 10/1990 | Solter | 374/5 X |
| 5,031,456 | 7/1991 | Askwith et al. | 374/5 |

FOREIGN PATENT DOCUMENTS

3616220A1 11/1987 Germany .
3-24449 2/1991 Japan .
3-82944 4/1991 Japan .

OTHER PUBLICATIONS

Transcript of Lectures of 29th Airplane Symposium, 1991, pp. 390-393.
Hagemaier, D. J., "Thermal Insulation Moisture Detection," Materials Evaluation, pp. 55-60 (Mar. 1970).
Lotti, Franco et al., "Flaw Recognition in Composite by Processing Sequences of Infrared Images", Accession No. 3810768, Abstract; and *Time-Varying Image Processing and Moving Object Recognition*, 2, Proceedings of the 3rd Intl. Workshop, Amsterdam, NL, pp. 232-240. (1990).
S. E. Cohen, "The Design and Application of the Traversing Infra-red Inspection System-TIRIS", *Non-Destructive Testing*, V. 6, No. 2, Apr. 1973, UK, pp. 74-80.
Patent Abstracts of Japan, V. 11, No. 201 (P-590) Jun. 30, 1987, and JP62024134, Mitsui Eng & Shipbuild Co. Ltd. (only abstract considered).

*Primary Examiner*—Diego F. F. Gutierrez
*Attorney, Agent, or Firm*—Oliff & Berridge

[57] ABSTRACT

To improve the detection precision and detection efficiency and further to automatize the detection process, moisture in a honeycomb panel is detected as follows: the honeycomb panel is heated by a lamp; the surface temperature of the heated construction is measured by an infrared radiation thermometer; the measured temperature is displayed to roughly discriminate an abnormal portion (i.e., a portion containing moisture); the honeycomb panel is further heated continuously to detect temperature-change-rates at both abnormal and normal portions (i.e., a portion not containing moisture); and the two temperature-change-rates are compared with each other to discriminate a presence of moisture.

7 Claims, 10 Drawing Sheets

METHOD FOR DETECTING MOISTURE IN A HONEYCOMB PANEL

BACKGROUND OF THE INVENTION

1. Field of the Invention

The present invention relates to a method of and a system for detecting moisture in a honeycomb panel such as an aircraft body, for instance.

2. Description of the Prior Art

In a honeycomb panel such as wings of an airplane, there exists a problem in that moisture included in the air enters the honeycomb panel due to repeated flights or due to change in atmospheric pressure, and further dew condensation occurs locally therewithin. The moisture in the honeycomb panel will be frozen when the airplane makes a flight at a high altitude, and bonded portions between the honeycomb panel and an outer plate are peeled off due to volumetric expansion of moisture at freezing, thus causing the honeycomb panel to be damaged when the local disbond propagates. As used in this specification and in the claims, a normal portion of a honeycomb panel is a portion containing no moisture and an abnormal portion is a portion containing moisture.

To overcome the above-mentioned problem conventionally, various techniques such as radiographical inspection by X rays, non-destructive test by ultrasonic waves, etc. have been so far adopted.

In addition, as one of the techniques of solving the above-mentioned problem, such a method of detecting moisture in an airplane honeycomb structure has been proposed that infrared images of an airplane structure and onboard appliances are taken with the use of an infrared image forming apparatus in order to inspect the normal and abnormal conditions of the airplane body and the onboard appliances on the basis of the obtained infrared images, as disclosed in Transcript of Lectures (1991) of 29th Airplane Symposium (Oct. 8, 1991) in Japan.

In this moisture inspection method, abnormal portions of the honeycomb panel are detected as follows: still images of the surfaces of the honeycomb panel are previously taken by use of the infrared image forming apparatus; integration images (summation images) are obtained by taking a plurality of infrared images after the airplane has landed and thereby the temperature of the airplane rises; and the integration images are compared with the still images to detect abnormal portions of the honeycomb panel. Further, in the above-mentioned Symposium, a technique of taking infrared images of an object to be inspected after instantaneous heating and cooling has been also proposed.

Further, another non-destructive inspection method for a bonded structure has been disclosed in Japanese Published Unexamined Patent Application Nos. 3-24449 and 3-82944, in which a structure formed by bonding thin plates is heated up to a predetermined temperature, and the surface temperature distribution during cooling process is measured on the basis of an infrared image in order to discriminate defective positions of the bonded portions.

The above-mentioned prior art methods of detecting moisture in a honeycomb panel involve various drawbacks as follows: In the case of the non-destructive inspection by the radiographical inspection (X rays), a radioactive ray source is required and therefore the handling is not safe; a specific film is required for inspection and therefore the inspection is costly; the workability of moisture detection is low and further the automatization of the moisture detecting method is rather difficult to realize; and it is impossible to detect such a small amount of moisture if each cell of the honeycomb panel is not perfectly filled with moisture, etc. In more detail, in the radiographical measurement based upon a difference in film density for instance, where a plurality of cell samples of a honeycomb panel are prepared and further cells including water are photographed by X rays, a difference in film density between the normal cells including no water and the abnormal cells filled with water is relatively large and therefore distinguishable. However, a difference in film density between the normal cells including no water and the abnormal cells having water partially is relatively small and therefore is difficult to be distinguished.

In the case of the non-destructive inspection by ultrasonic waves, an inspector skilled in the measurement is required; the workability of moisture detection is low; the automatization of moisture detection is difficult; it is difficult to detect a small amount of moisture, etc.

In the case of the moisture inspection due to infrared images, since still images must be previously photographed, it is rather difficult to apply this method to various honeycomb panels other than a specific structure. In addition, since the infrared images are taken when the temperature of the airplane rises after landing, it is difficult to detect a small amount of moisture. This is because a difference in temperature between normal and abnormal portions is small and additionally the detection is subjected to the influence of noise, so that the detection precision is deteriorated, with the result that the resolution power of temperature detection is as low as about 0.3° to 0.5° C.

SUMMARY OF THE INVENTION

With these problems in mind therefore, it is the object of the present invention to provide a method of and a system for detecting moisture in any given honeycomb panels, which is high in detection precision and workability and further which can be automatized.

To achieve the above-mentioned object, the method of detecting moisture in a honeycomb panel according to the present invention comprising the steps of: heating a honeycomb panel continuously from the outside without direct contact with the honeycomb panel; measuring temperature on a surface of the heated honeycomb panel; and detecting moisture in the honeycomb panel on the basis of the measured temperature.

The temperature on the surface of the heated honeycomb panel is measured when a predetermined time has elapsed after a start of the heating. A presence of moisture is detected on the basis of a difference in temperature or in temperature change rate between an abnormal portion and a normal portion. Further, the method of the present invention comprises the steps of obtaining infrared image signals on the basis of the measured temperature; binarizing the obtained infrared image signals; and detecting the moisture on the basis of the binarized infrared image signals.

Further, the method of detecting moisture in a honeycomb panel according to the present invention comprises the steps of: heating a honeycomb panel; measuring temperature on a surface of the honeycomb panel by an infrared radiation thermometer; obtaining infrared image signals on the basis of the measured temperature;

displaying the obtained infrared image signals; discriminating an abnormal portion on the displayed infrared image; continuously heating the honeycomb panel while continuously measuring temperatures at both abnormal and normal portions; and detecting a presence of moisture at the abnormal portion on the basis of comparison in temperature change rate between the abnormal and normal portions.

In the method of detecting moisture in a honeycomb panel according to the present invention, since the honeycomb panel is continuously heated without direct contact with the honeycomb panel, it is possible to measure a difference in temperature between abnormal (including moisture) and normal (including no moisture) portions after the panel has been heated sufficiently, thus improving the moisture detection precision. Further, in the present invention, since it is unnecessary to previously take a photograph of the honeycomb panel, it is possible to apply the method of the present invention to any kinds of honeycomb panels.

Further, since the construction can be heated without direct contact with the heating means and the temperature of the heated structure can be measured by the infrared radiation thermometer, it is possible to allow the moisture detection work according to the present invention to be simple, efficient, and low in cost and further automatizable.

Further, since the surface temperature is measured when a predetermined time has elapsed after the start of the heating, it is possible to measure a sufficiently high difference in temperature between the abnormal and normal portions, thus improving the detection precision.

Further, since the detected temperature data are converted into infrared image signals and further binarized into binary data, it is possible to automatically detect moisture for each section of the honeycomb panel.

In the case where visible light is used as means for heating the honeycomb panel, it is possible to use the heating light as the illumination light at a low cost. Further, in the case where infrared light is used as means for heating the construction, it is possible to reduce the heating time and thereby to improve the detection workability.

Further, when the infrared image is displayed on a display unit, it is possible to roughly locate the abnormal positions, thus improving the detection efficiency for the succeeding fine and precise detection.

Further, in the case where the honeycomb panel is heated continuously; the temperatures at abnormal and normal portions are measured continuously; and the temperature change rates at the abnormal and normal portions are compared with each other to detect the temperature at the abnormal portions, since a small amount of moisture can be detected securely as a difference in temperature-change-rate, it is possible to detect the presence of moisture at high precision.

DETAILED DESCRIPTION OF THE PREFERRED EMBODIMENTS

A first embodiment of the method of detecting moisture in a honeycomb panel according to the present invention will be described hereinbelow with reference to the attached drawings.

Prior to the description of the first embodiment, a detecting system applied to the method according to the present invention will be described hereinbelow in detail.

Figure 1:
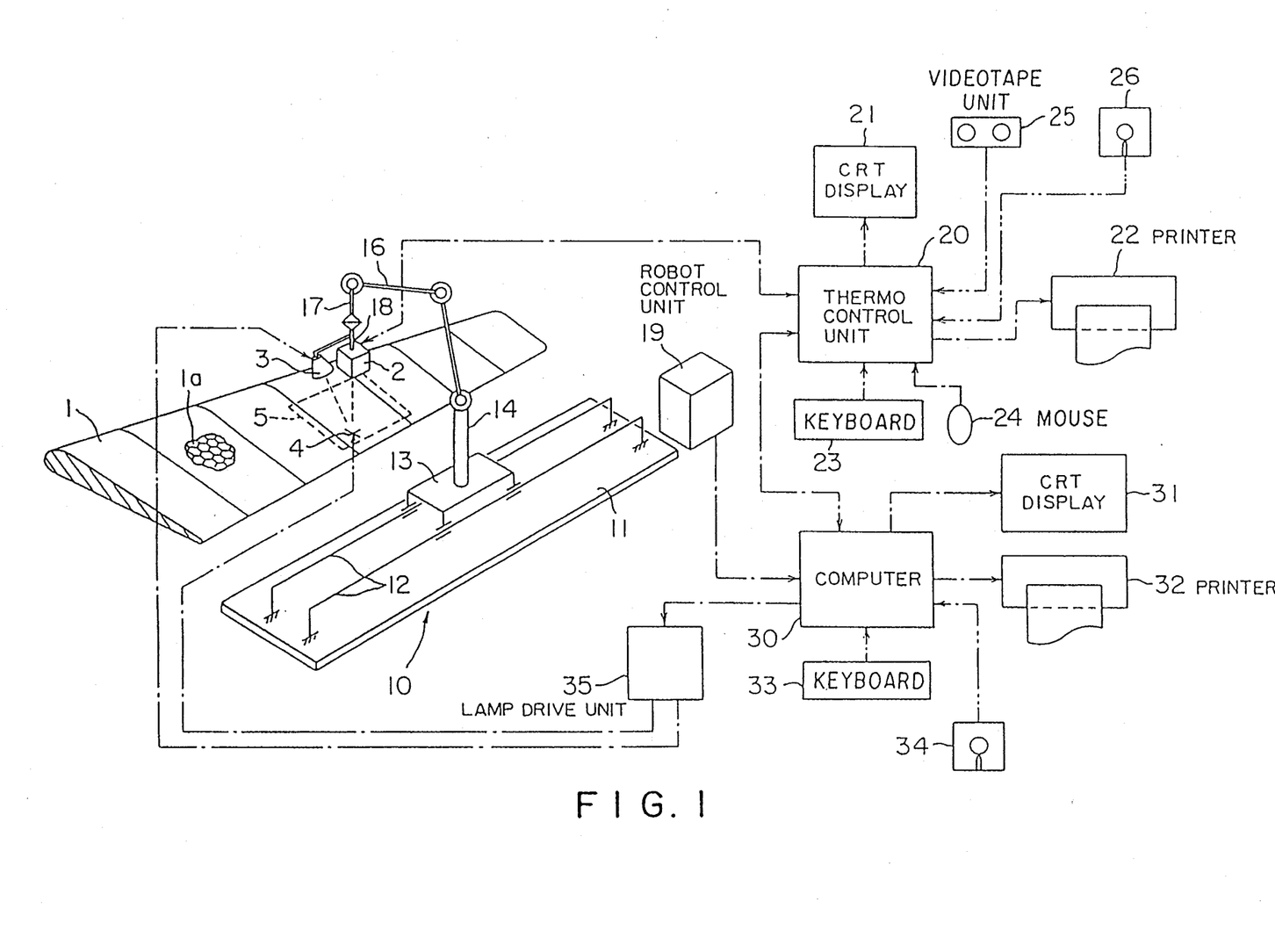
FIG. 1 is a block diagram showing a system of the present invention for detecting moisture in a honeycomb panel.

In FIG. 1, the system comprises roughly an infrared radiation thermometer (temperature measuring means) 2, an incandescent lamp 3 (heating means), a multi-joint orthogonal coordinate 5-axis robot 10, a thermometer control unit 20, a lamp drive unit 35, a robot control unit 19, a computer 30, etc.

The infrared radiation thermometer 2 and the incandescent lamp 3 are botch located over an upper surface of an airplane wing 1 a predetermined distance away from the wing 1 in order to detect moisture included in a honeycomb panel 1a of the airplane wing 1. The infrared radiation thermometer 2 and the incandescent lamp 3 are supported by a hand 18 of the multi-joint orthogonal 5-axis robot 10 so as to be movable in three dimensional way.

The robot 10 is composed of a base 11 extending in the longitudinal direction of the wing 1 and movable relative to the floor, a pair of ball screw guide shafts 12 fixed to and extending along the base 11, a movable base member 13 movable along the guide shaft 12 under numerical control, a column 14 arranged vertically on the movable base member 13, a first arm 15, a second arm 16, a third arm 17, and the hand 18, whose structure is of ordinary structure. The robot 10 is controlled by the robot control unit 19.

The infrared radiation thermometer 2 is controlled by the infrared radiation thermometer control unit 20, to which a CRT display unit 21, a color printer 22, a keyboard 23, a mouse 24 for moving a cursor on a picture when the display unit 21 are connected. In addition, a video tape driving unit 25 for recording data to a video tape 25 and a floppy disk driving unit 26 for recording data to a floppy disk 26 are connected to the thermometer control unit 20.

The thermometer control unit 20 is connected to the computer 30, to which a CRT display unit 31, a printer 32, a keyboard 33, a floppy disk driving unit 34 for driving a floppy disk, etc. are connected. Further, the computer 30 is connected to the robot control unit 19 and the lamp drive unit 35. A control program for controlling the robot 10 via the robot control unit 19 and other programs for controlling the thermometer control unit 20 and the lamp drive unit 35 are all previously stored in the computer 30.

The method of detecting the moisture in the honeycomb panel of the wing 1 with the use of the above-mentioned moisture detecting system will be described.

In a first step, the robot 10 is actuated in accordance with a command transmitted from the computer 30 through the robot control unit 19, so that the infrared radiation thermometer 2 and the incandescent lamp 3 are both moved over the surface of the wing 1 (an object to be measured).

In a second step, a reference position mark (an origin of coordinates) 4 is set by use of a cross-shaped heater at a predetermined marked position within a small section (area) 5 of the portion to be measured, and current is passed through the cross-shaped heater now set. The small section to be measured 5 is heated for a predetermined time by the incandescent lamp 3; the surface temperature of the heated small section 5 is photographed by the infrared radiation thermometer 2 to obtain an infrared image; the image signals of the photographed infrared image are transmitted to the thermometer control unit 20; and the transmitted image signals are displayed on the display unit 21.

In a third step, the infrared image displayed on the display unit 21 is checked on the basis of the color and the pattern thereof by visual inspection, in order to detect a single or a plurality of abnormal positions on the surface of the honeycomb panel.

Figure 2:
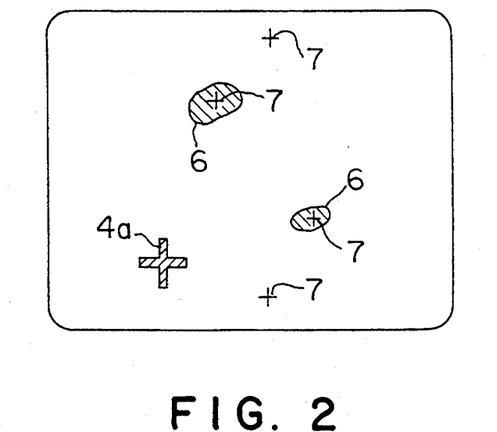
FIG. 2 is an illustration for assistance in explaining a picture displayed on a display unit, in which measurement points have been determined on the basis of a reference mark.

In a fourth step, the cursor is moved at the abnormal position by use of the mouse 24. Under these conditions, the abnormal position is set as a measurement point by transmitting a command from the keyboard 23 to the thermometer control unit 20. Further, in the case of presence of a plurality of abnormal portions, the above-mentioned procedure is repeated to set the plural abnormal points as the measurement points. In this case, the reference mark 4 is also set as the measurement point. Further, it is possible to set another basic position or a normal portion as the measurement points. In the case of the thermometer 20 shown in FIG. 1, ten measurement points for instance can be set. FIG. 2 shows an example of the picture on the display unit 21, in which two abnormal portions 6, the reference mark 4a and four measurement points 7 are determined and shown.

Further, after the measurement points have been set, the displayed infrared image is printed by the color printer 22.

In a fifth step, the incandescent lamp 3 is lit up by the command transmitted from the computer 30 through the lamp drive unit 35 to heat the small section 5 to be measured (the same way as that in step 2 above) further continuously, and the reference mark 4 is further heated. The temperatures at a plurality of the measurement points set in the fourth step are measured continuously by the infrared radiation thermometer 2 in time series fashion. The obtained time-series temperature signals are A/D converted by the thermometer control unit 20 and the converted digital signals are supplied to the computer 30 in time series fashion.

In a sixth step, the supplied temperature data at the plural measurement points are analyzed in accordance with an analyzing program previously stored in the computer 30 in order to discriminate whether moisture is included in the single or plural abnormal portions already set in the fourth step.

In this analysis, the temperature-change-rates at the signal or plural normal portions are calculated, and the temperature-change-rates at the respective abnormal portions are also calculated. When the temperature-change-rate at the abnormal portion is distinctly smaller than those at the normal portions, the abnormal portion is determined as that moisture is present. On the other hand, when there exists no substantial difference in the temperature-change-rate between the abnormal portion and the normal portions, the abnormal portion is determined as that moisture is absent.

The reason is as follows: in the case where water fills or attaches to a single or plural hexagonal cells of the honeycomb panel, the temperature-change-rate at the abnormal portion is securely small as compared with the temperature-change-rate at the normal portion due to the influence of the latent heat of moisture evaporation, so that it is possible to detect the presence or absence of moisture at the abnormal portions.

Further, since the difference in temperature between the normal and abnormal portions increases more after the measurement points have been heated continuously, it is preferable to detect the presence or absence of moisture at the abnormal portions on the basis of the temperature difference obtained after the object to be measured has been heated for a long time continuously.

Figure 3:
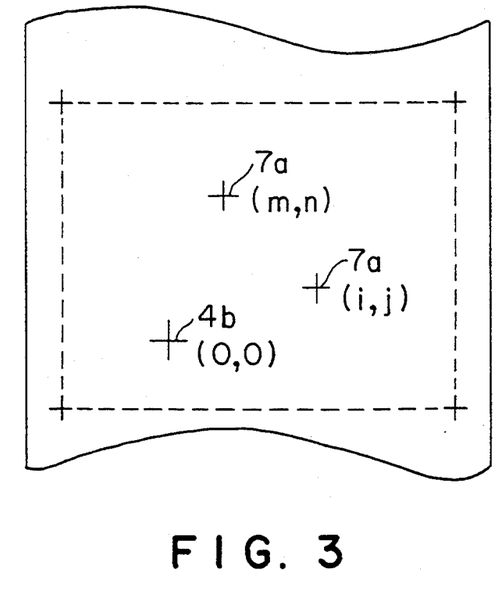
FIG. 3 is an illustration for assistance in explaining an example of printed out paper in which abnormal points including moisture are indicated in a coordinate system.

In a seventh step, the measurement points of the abnormal portions (in which moisture is present) are located in relation to the reference mark 4 by calculations on the basis of the positional data representative of the measurement points set in the fourth step, the data with respect to the abnormal portions (in which moisture is included) obtained by the analyzed results in the sixth step, and the control data (including the positional data representative of the location of the hand 18 of the robot 10) supplied from the robot control unit 19. FIG. 3 shows an example in which a reference mark 4b, two measurement points 7a of the abnormal portions including moisture are shown together with the positional information data (coordinates: (m, n) or (i, j)) of the abnormal measurement points 7a with the reference mark 4b (0, 0) as an origin of the coordinates. These data are all printed by the printer 32. Further, in the above-mentioned calculation step, the calculation control programs are all previously stored in the computer 30.

As described above, since a mark at which the reference mark 4 is set is printed in the small section 5 on the wing 1 to be measured, it is possible to accurately know the positions and the areas of the abnormal portions including moisture within the small section 5 to be measured on the wing 1.

The test results of the method of detecting the moisture in the honeycomb panel will be described with reference to FIGS. 4 to 15.

[Over surface heating]

Figure 4:
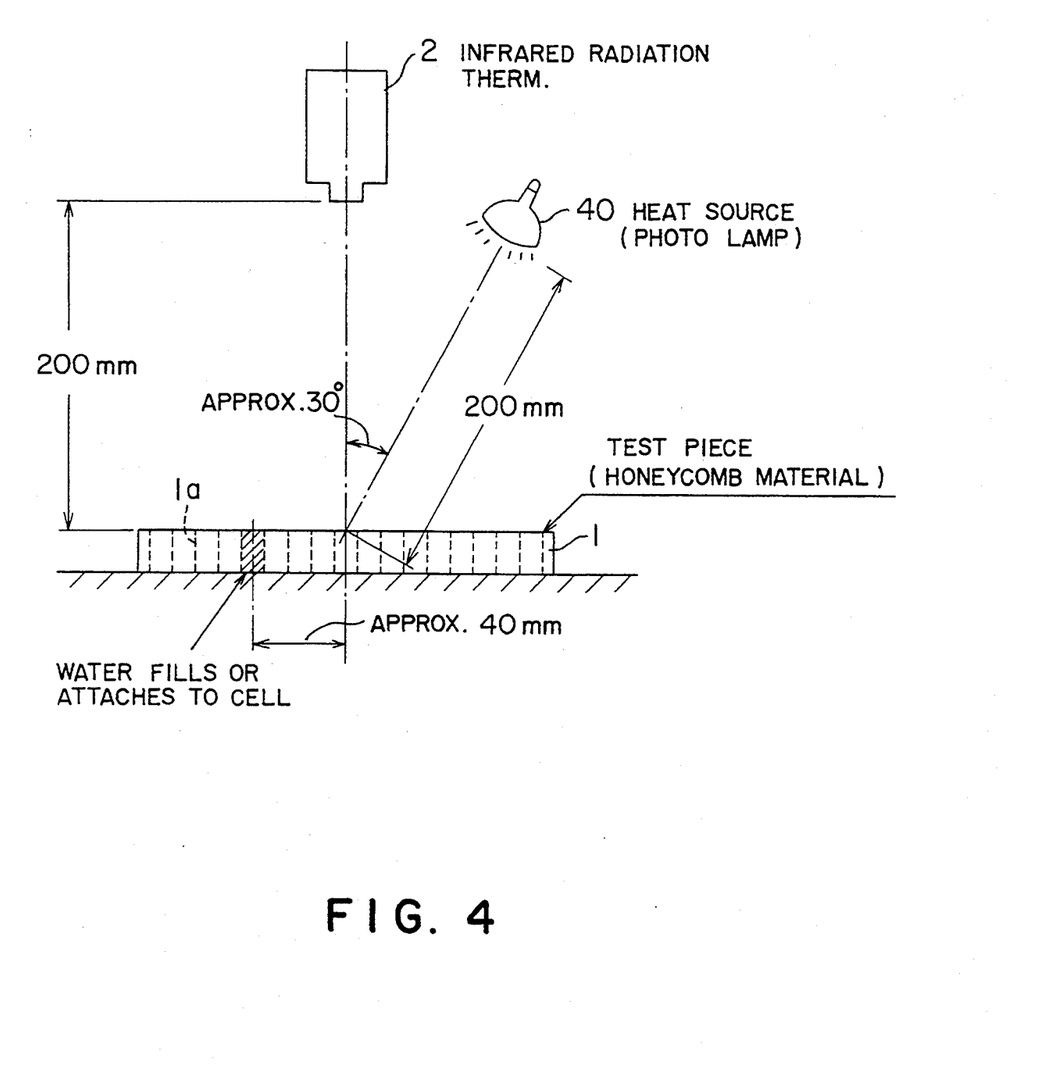
FIG. 4 is an illustration for assistance in explaining the method of measuring temperature on the upper surface of a test piece heated by over surface heating.

As shown in FIG. 4, the infrared radiation thermometer 2 and a photographic lamp 40 were arranged over the honeycomb material (test piece) 1. The case where the honeycomb material 1 is heated from above by the photographic lamp 40 is defined as over surface heating. The test was made for both the cases where water fills and attaches to the cell Of the honeycomb material 1.

Figure 5:
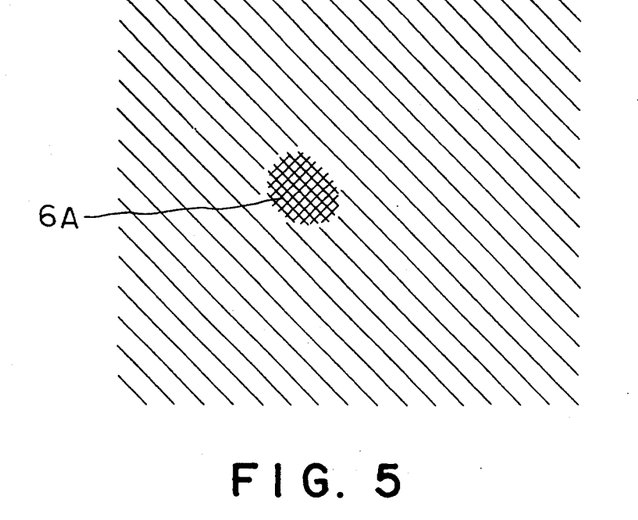
FIG. 5 is an illustration for assistance in explaining an infrared image displayed on a display unit, when water fills a cell.
Figure 7:
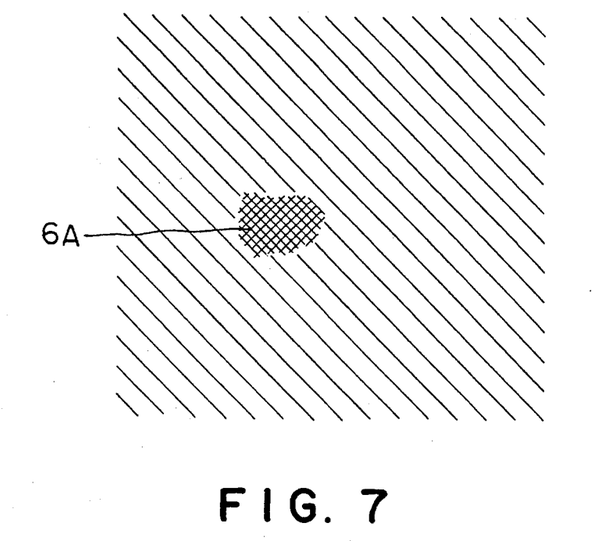
FIG. 7 is an illustration for assistance in explaining the infrared image displayed on the display unit, when water attaches to a cell.

FIG. 5 is an infrared image obtained when water fills a cell in the fourth step, in which an abnormal portion 6A is shown by meshes and the remaining normal portion is shown by a hatch. FIG. 7 is an infrared image obtained when water attaches to a cell in the fourth step, in which an abnormal portion 6A is shown by meshes and the remaining normal portion is shown by a hatch.

Figure 6:
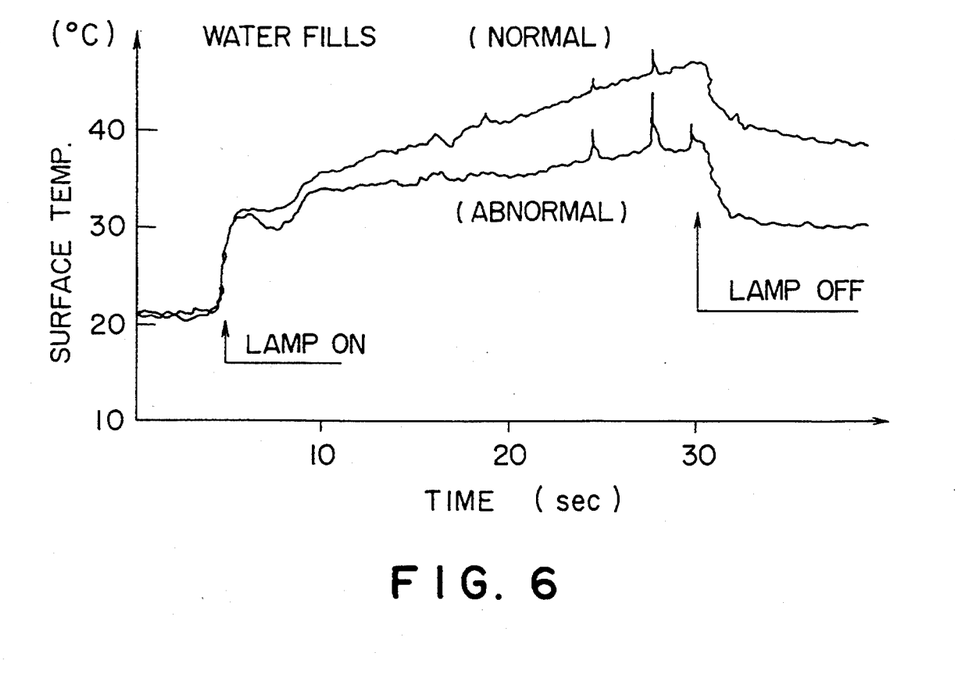
FIG. 6 is a graphical representation showing temperature change rate characteristics of both normal and abnormal portions, when water fills a cell.
Figure 8:
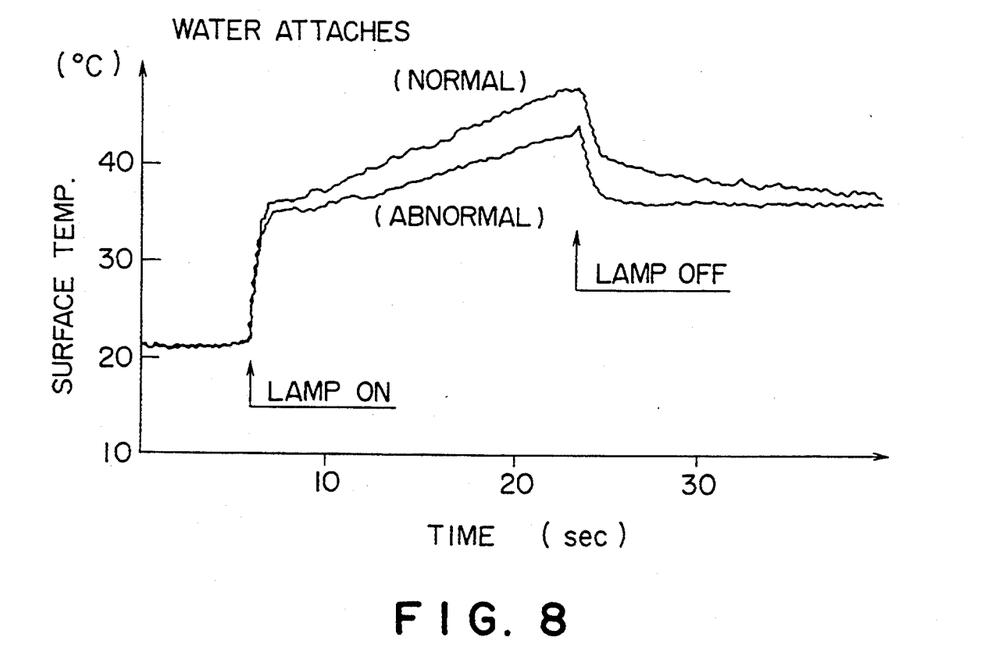
FIG. 8 is a graphical representation showing temperature change rate characteristics of both normal and abnormal portions, when water attaches to a cell.

Further, FIG. 6 is a temperature characteristic diagram obtained when water fills a cell in the fifth step, in which the temperature variation is shown for both the normal and abnormal portions heated continuously after the measurement points have been set in the infrared image as shown in FIG. 5. FIG. 8 is a temperature characteristic diagram obtained when water attaches to a cell in the fifth step, in which the temperature variation is shown for both the normal and abnormal portions heated continuously after the measurement points have been set in the infrared image as shown in FIG. 7.

The above test results indicate that the temperature-change-rate at the abnormal portions is smaller than that at the normal portions, for both the cases where water fills and attaches to the cell.

[Under surface heating]

Figure 9:
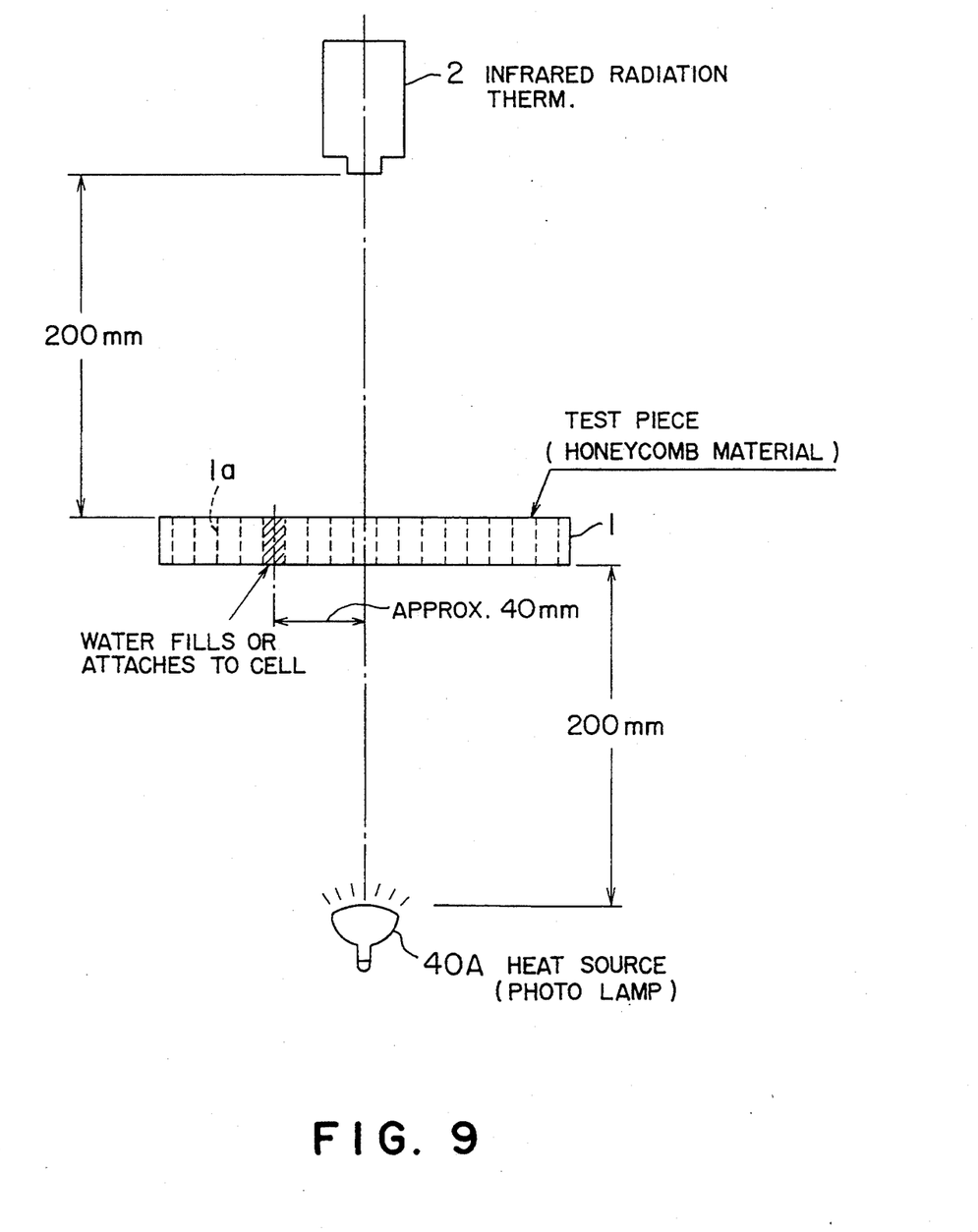
FIG. 9 is an illustration for assistance in explaining the method of measuring temperature on the lower surface of a test piece heated by under surface heating.

As shown in FIG. 9, the infrared radiation thermometer 2 was arranged over the honeycomb material (test piece) 1 and a photographic lamp 40A was arranged under the honeycomb material 1. The case where the honeycomb material 1 is heated from below by the photographic lamp 40A is defined as under surface heating. The test was made for both the cases where water fills and attaches to the cell of the honeycomb material 1. The test was conducted on a honeycomb material test piece 1 which includes water. The test is conducted to confirm the results of the present invention.

Figure 10:
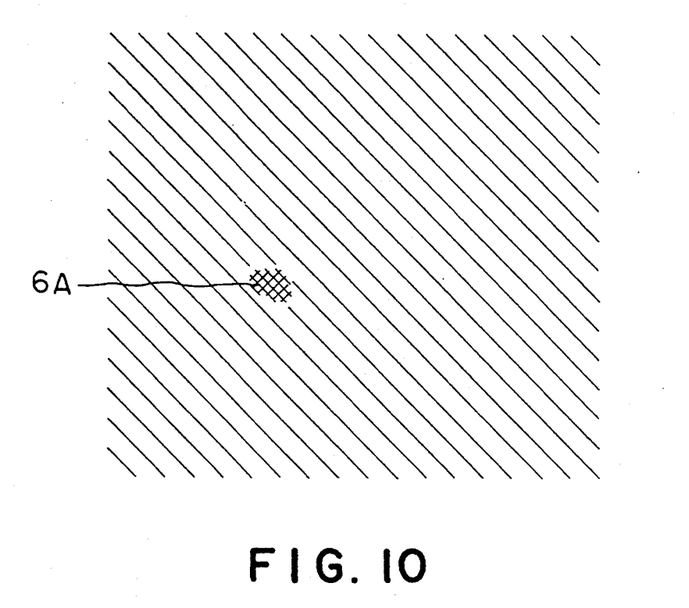
FIG. 10 is an illustration for assistance in explaining an infrared image displayed on a display unit, when water fills a cell.
Figure 12:
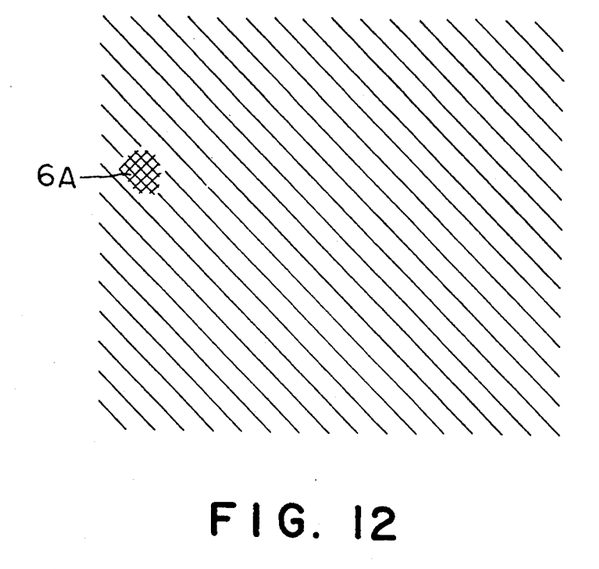
FIG. 12 is an illustration for assistance in explaining the infrared image displayed on the display unit, when water attaches to a cell.

FIG. 10 is an infrared image obtained when water fills a cell in the fourth step, in which an abnormal portion 6A is shown by meshes and the remaining normal portion is shown by a hatch. FIG. 12 is an infrared image obtained when water attaches to a cell in the fourth step, in which an abnormal portion 6A is shown by meshes and the remaining normal portion is shown by a hatch. Further, in this test since the test temperature was lower than that in the over surface heating test, the cell patterns of the honeycomb material were observed. However, these patters are omitted in FIGS. 10 and 12.

Figure 11:
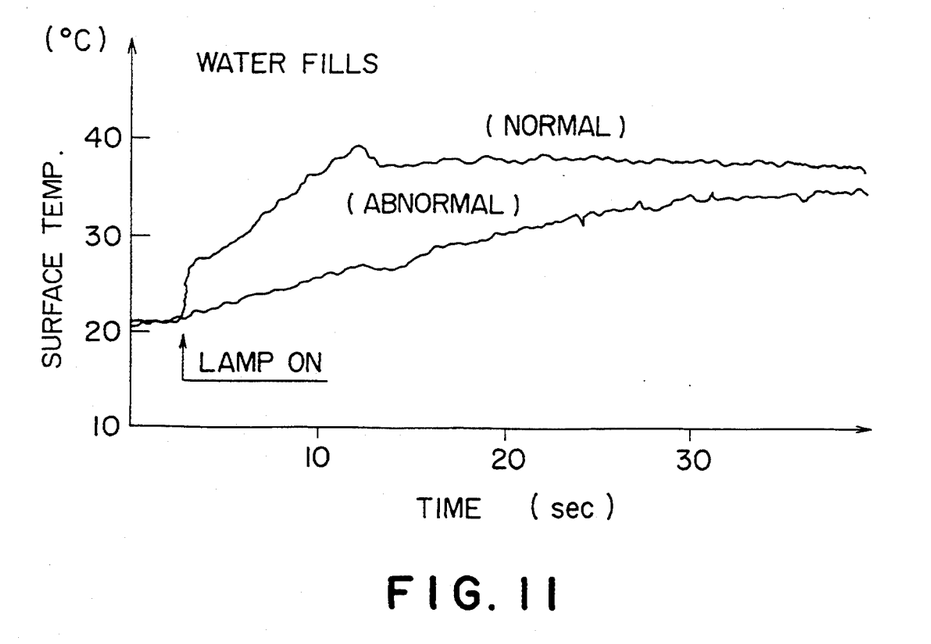
FIG. 11 is a graphical representation showing temperature change rate characteristics of both normal and abnormal portions, when water fills a cell.
Figure 13:
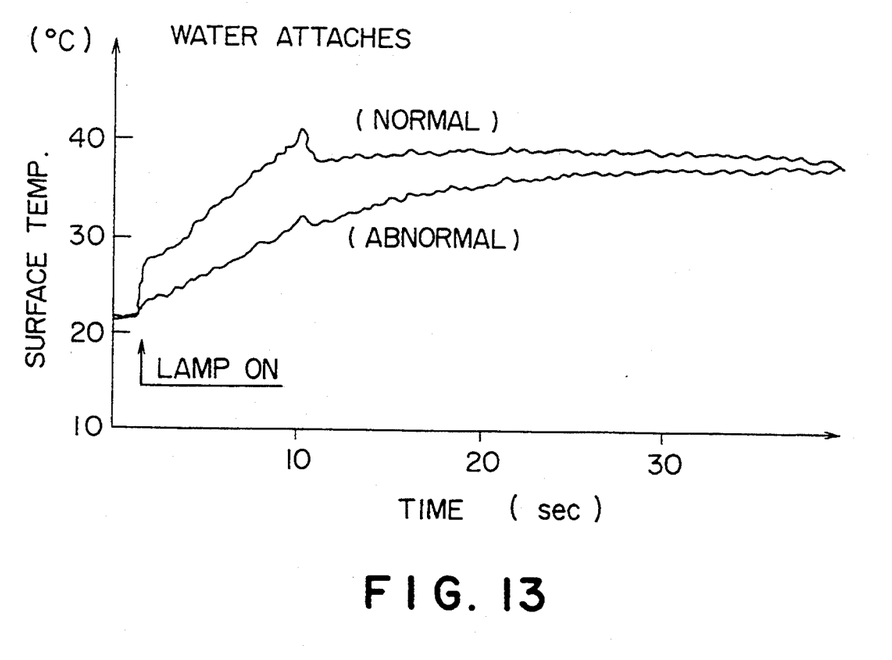
FIG. 13 is a graphical representation showing temperature-change-rate characteristics of both normal and abnormal portions, when water attaches to a cell.

Further, FIG. 11 is a temperature characteristic diagram obtained when water fills a cell in the fifth step, in which the temperature variation is shown for both the normal and abnormal portions heated continuously after the measurement points have been set in the infrared image as shown in FIG. 10. FIG. 13 is a temperature characteristic diagram obtained when water attaches to a cell in the fifth step, in which the temperature variation is shown for both the normal and abnormal portions heated continuously after the measurement points have been set in the infrared image as shown in FIG. 12.

The above test results indicate that the temperature-change-rate at the abnormal portions is smaller than that at the normal portions, for both the cases where water fills and attaches to the cell.

Figure 14:
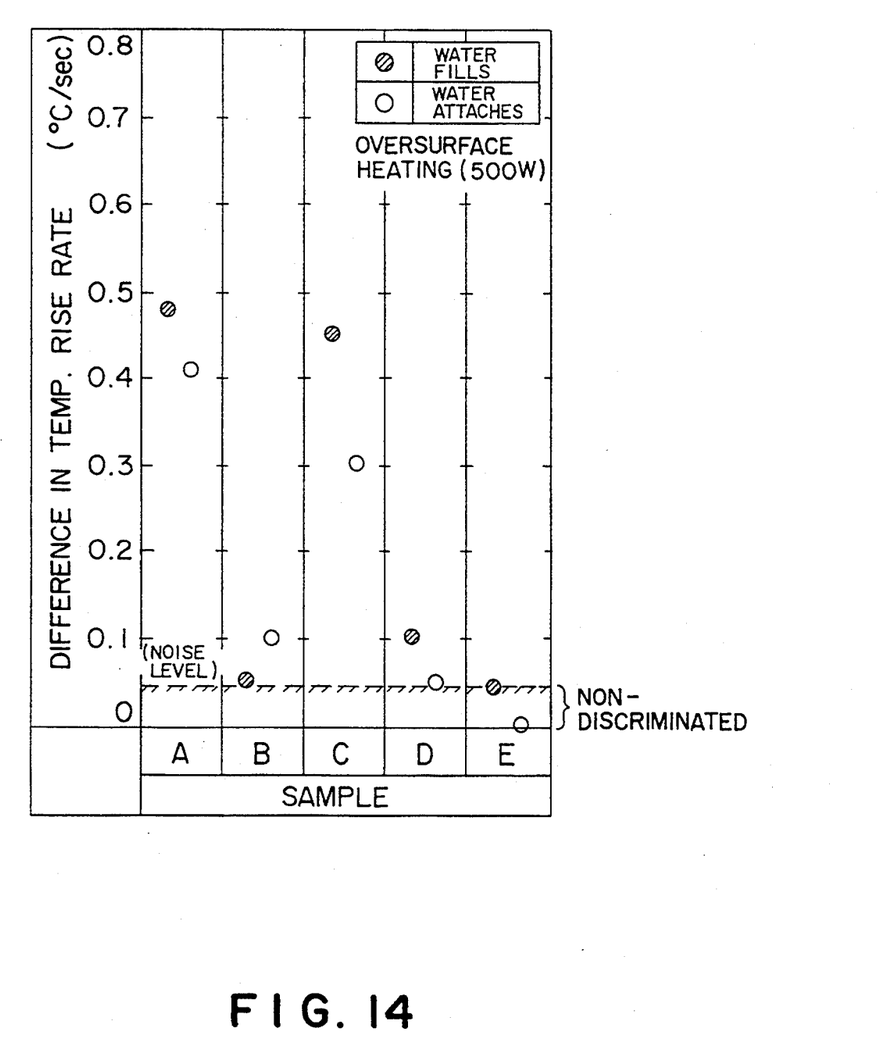
FIG. 14 is a graphical representation showing difference in temperature-rise-rate among five test samples, in which both the cases where water fills and attaches to a cell are shown.
Figure 15:
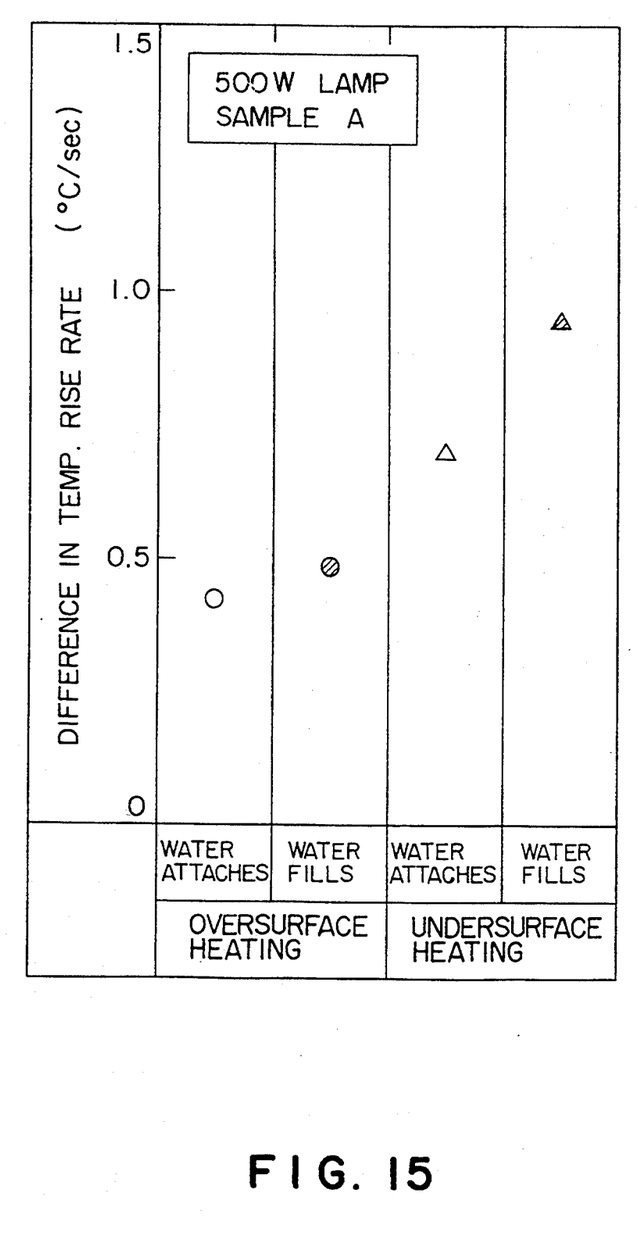
FIG. 15 is a graphical representation showing a difference in temperature-rise-rate of a test sample A between the upper and under surface heatings, in which both the cases where water fills and attaches to a cell are shown.

Further, five test samples A, B, C, C, D of honeycomb panel (composite honeycomb materials made of different FRPs (fiber reinforced plastics)) were prepared. The tests the same as above (over and under surface heating tests for both when water fills and attaches to the cell) were made for these test samples by use of an incandescent lamp of 500 W as heating means. FIG. 14 shows differences in temperature-rise-rate between the normal and abnormal portions of five test samples A to D in the over surface heating test, in which the hatched circles designate the case where water fills the cell and the circles designate the case where water attaches to the cell. FIG. 15 shows the differences in temperature-rise-rate between the normal and abnormal portions of the test sample A in both over and under surface heating tests, in which the hatched circle and hatched triangular designate the case where water fills the cell and the circle and triangular designate the case where water attaches to the cell.

A second embodiment of the method of detecting moisture in the honeycomb panel will be described hereinbelow.

The first and fourth steps are quite the same as those of the first embodiment, so that these steps are omitted herein.

In a fifth step, the incandescent lamp 3 is lit up by the command transmitted from the computer 30 through the lamp drive unit 35 to continuously heat the small section 5 to be measured (the same as that in step 2 above), and further the reference mark 4 is heated by flowing current therethrough. The temperatures at a plurality of the measurement points set in the fourth step are measured by the infrared radiation thermometer 2 when a predetermined time has elapsed (e.g., 10 sec) after the start of the continuous heating. Further, the infrared images are printed by the color printer 22. However, it is possible to omit the above-mentioned temperature measurement and the printing by the color printer 22 in this fifth step.

In the sixth step, the small section 5 is kept heated continuously from the preceding step, and after a predetermined time (e.g., 15 to 20 sec) has elapsed after the start of the continuous heating in the preceding step, the temperatures at a plurality of the measurement points set in the fourth step are measured by the infrared radiation thermometer 2. The obtained infrared image signals are A/D converted by the thermometer control unit 20 and the converted signals are supplied to the computer 30. Here, the above-mentioned predetermined time elapsed is a time point when a difference in temperature between the normal and abnormal portions increases sufficiently (e.g., the temperature at the normal portion is about 5° C. higher than that at the abnormal portion)

and additionally the infrared image becomes light pink or white (at about 45° to 50° C.) in color at the normal portions and dark red or dark pink (at about 40° to 45° C.) at the abnormal portions.

In the seventh step, the obtained temperature data are binarized on the basis of a predetermined threshold by the computer 30 in accordance with a predetermined program, and any abnormal portions in which moisture is included are detected on the basis of the obtained binary data.

In any eighth step, the position of the abnormal portions relative to the reference mark 4 are calculated on the basis of the positional data of the measurement points set in any fourth step, the data related to the abnormal portions obtained as the result of the seventh step, and control data supplied by the robot control unit 19 (including the positional data of the hand 18 of the robot 10). The reference mark, the abnormal portions including moisture and the positional information (coordinates) of the abnormal portions as shown in FIG. 3 are all printed by the printer 32.

As described above, in the method of detecting moisture in a honeycomb panel according to the present invention, it is possible to detect the abnormal portions including moisture by continuously heating the honeycomb panel from the outside to increase a difference in temperature between the normal and abnormal portions without direct contact with an object to be measured, by measuring the temperatures at both the normal and abnormal portions with the use of the infrared radiation thermometer, and by comparing the temperatures or the temperature-change-rates between both the normal and abnormal portions. In addition, it is possible to detect the moisture by a high speed processing within a short time and to automatize the moisture detection processing, so that the moisture detecting cost can be reduced markedly.

In particular, since the reference mark is set within the section to be measured, it is possible to locate the abnormal portion in the form of coordinates on the basis of the reference mark (the origin of the coordinate axes).

Further, an infrared heating apparatus can be used as the heating means instead of the incandescent lamp. Further, the various reference marks heated to a high or low temperature can be used as far as the temperature at the reference mark is distinguishable from the temperature at the normal and abnormal portions. Further, the system and method of detecting moisture according to the present invention can be applied to various honeycomb panels other than the wings of an airplane and various honeycomb panels other than aircraft.

What is claimed is:

1. A method of detecting moisture in a honeycomb panel, comprising the steps of:
    applying a reference position mark heater at a reference marking position within a predetermined area of a surface of the honeycomb panel;
    energizing the reference position mark heater;
    heating the predetermined area;
    photographing the predetermined area, including the reference position mark heater, with an infrared radiation thermometer to obtain infrared image signals of said predetermined area and said reference position mark heater;
    displaying an infrared image of said predetermined area and said reference position mark heater;
    discriminating abnormal portions of the predetermined area containing moisture on the displayed infrared image;
    continuously heating the predetermined area while continuously displaying the infrared images of both abnormal portions containing moisture and normal portions free from moisture;
    measuring temperature-related characteristics of the abnormal portions and the normal portions;
    detecting the presence of moisture at the abnormal portions on the basis of comparisons between the temperature-related characteristics of the abnormal portions and the temperature-related characteristics of the normal portion; and
    locating the abnormal portions in the form of coordinates on the basis of said displayed infrared image of said reference position mark heater.

2. The method of detecting moisture in a honeycomb panel of claim 1, wherein said step of measuring temperature-related characteristics is carried out when a predetermined time has elapsed after a start of said step of heating.

3. The method of detecting moisture in a honeycomb panel of claim 1, wherein said temperature-related characteristics are temperatures.

4. The method of detecting moisture in a honeycomb panel of claim 3, wherein said comparisons are made by detecting a difference in temperature between the abnormal portions and the normal portions.

5. The method of detecting moisture in a honeycomb panel of claim 1, wherein said temperature-related characteristics are temperature-change rates.

6. The method of detecting moisture in a honeycomb panel of claim 5, wherein said comparisons are made by detecting a difference in temperature-change rates between the abnormal portions and the normal portions.

7. The method of detecting moisture in a honeycomb panel of claim 1, wherein said step of measuring temperature related characteristics is repeated a plurality of times in a time series fashion.

* * * * *

UNITED STATES PATENT AND TRADEMARK OFFICE
CERTIFICATE OF CORRECTION

PATENT NO. : 5,433,106
DATED : July 18, 1995
INVENTOR(S) : Hiroyuki Matsumura; Takamasa Ogata; Hideyuki Hirasawa; Masato Uchiyama; and Kenji Tsubaki It is certified that error appears in the above-indentified patent and that said Letters Patent is hereby corrected as shown below:

<u>On the Cover Page</u>:

[73] Assignee: Kawasaki Jukogyo <u>Kabushiki</u> Kaisha, Hyogo, Japan

Signed and Sealed this

Nineteenth Day of December, 1995

*Attest:*

BRUCE LEHMAN

*Attesting Officer*     *Commissioner of Patents and Trademarks*